United States Patent [19]
Knowlton

[11] Patent Number: 5,871,524
[45] Date of Patent: Feb. 16, 1999

[54] APPARATUS FOR CONTROLLED CONTRACTION OF COLLAGEN TISSUE

[75] Inventor: Edward W. Knowlton, Danville, Calif.

[73] Assignee: Thermage, Inc., Alamo, Calif.

[21] Appl. No.: 794,003

[22] Filed: Feb. 3, 1997

Related U.S. Application Data

[62] Division of Ser. No. 435,544, May 5, 1995, Pat. No. 5,660,836.

[51] Int. Cl.$^6$ ........................................................ A61F 2/00
[52] U.S. Cl. .............................. 607/101; 606/27; 606/31; 607/102
[58] Field of Search ............................. 607/96, 100, 101, 607/97–99, 102–104; 128/897, 898; 606/2, 9, 33, 41; 600/373

[56] References Cited

U.S. PATENT DOCUMENTS

| | | | |
|---|---|---|---|
| Re. 32,849 | 1/1989 | Wei et al. ........................... | 204/192.27 |
| 3,831,604 | 8/1974 | Neefe . | |
| 4,074,718 | 2/1978 | Morrison ............................ | 128/303.14 |
| 4,140,130 | 2/1979 | Storm, III ............................... | 128/404 |
| 4,164,226 | 8/1979 | Tapper ................................. | 128/419 R |
| 4,290,435 | 9/1981 | Waggott .................................. | 128/800 |
| 4,343,301 | 8/1982 | Indech ....................................... | 128/24 |
| 4,346,715 | 8/1982 | Gammell ................................ | 128/422 |
| 4,375,220 | 3/1983 | Matvias .................................. | 128/804 |
| 4,381,007 | 4/1983 | Doss .................................... | 128/303.1 |
| 4,441,486 | 4/1984 | Pounds ...................................... | 128/24 |
| 4,545,368 | 10/1985 | Rand et al. ............................... | 128/1.3 |
| 4,676,258 | 6/1987 | Inokuchi et al. ........................ | 128/804 |
| 4,709,701 | 12/1987 | Weber ..................................... | 128/422 |
| 4,881,543 | 11/1989 | Trembly et al. ...................... | 128/303.1 |
| 4,887,614 | 12/1989 | Shirakami et al. ...................... | 128/798 |
| 4,889,122 | 12/1989 | Watmough et al. ..................... | 128/399 |
| 4,944,302 | 7/1990 | Hermandez et al. .................... | 128/798 |
| 4,957,480 | 9/1990 | Morenings ................................. | 604/20 |
| 4,962,761 | 10/1990 | Golden ..................................... | 128/400 |
| 4,976,709 | 12/1990 | Sand ........................................... | 606/5 |

(List continued on next page.)

FOREIGN PATENT DOCUMENTS

| | | |
|---|---|---|
| 0 519 415 | 12/1992 | European Pat. Off. . |
| 1 949 534 | 4/1970 | Germany . |
| 266678 | 12/1997 | New Zealand . |
| WO 92/19414 | 11/1992 | WIPO . |
| 93/13816 | 7/1993 | WIPO . |
| 94/26228 | 11/1994 | WIPO . |
| 96/27240 | 9/1996 | WIPO . |
| 96/27327 | 9/1996 | WIPO . |
| 96/32051 | 10/1996 | WIPO . |
| 96/34568 | 11/1996 | WIPO . |
| 96/39914 | 12/1996 | WIPO . |
| 97/18765 | 5/1997 | WIPO . |
| 97/18768 | 5/1997 | WIPO . |
| 68/03117 | 1/1998 | WIPO . |
| 98/03220 | 1/1998 | WIPO . |

OTHER PUBLICATIONS

Allain, et al. "Isometric Tensions Developed During the Hydrothermal Swelling of Rat Skin", Connective Tissue Research, vol. 7, pp. 697–701, (1990).

Danielson, C. "Age–Related thermal stability and susscep-tibility to proteolysis of rat bone collagen", . . . chem, Great Britain, pp. 697–701, (1990).

(List continued on next page.)

*Primary Examiner*—Michael Peffley
*Assistant Examiner*—Bryan K. Yarnell
*Attorney, Agent, or Firm*—Wilson Sonsini Goodrich & Rosati

[57] ABSTRACT

An apparatus applies radiant energy through the skin to an underlying subcutaneous layer or deeper soft tissue layers that includes loculations of fat with fibrous septae made of collagen tissue. This creates a desired contour effect without substantially modifying melanocytes and other epithelial cells in the epidermis. A membrane conforms a contacting exterior surface of the membrane to a skin layer. One or more thermal electrodes positioned in the membrane. A focussing element focuses thermal energy to the underlying collagen tissue. The focusing element and the electrolytic solution create a reverse thermal gradient from the skin to the collagen tissue. A thermal power source is coupled to the thermal electrodes.

38 Claims, 6 Drawing Sheets

U.S. PATENT DOCUMENTS

| | | | |
|---|---|---|---|
| 5,003,991 | 4/1991 | Takayama et al. | 128/784 |
| 5,133,351 | 7/1992 | Masaki | 128/419 R |
| 5,143,063 | 9/1992 | Fellner | 128/399 |
| 5,186,181 | 2/1993 | Franconi et al. | 128/804 |
| 5,190,517 | 3/1993 | Zieve et al. | 604/22 |
| 5,230,334 | 7/1993 | Klopotek | 128/399 |
| 5,249,575 | 10/1993 | DiMino et al. | 607/150 |
| 5,282,797 | 2/1994 | Chess | 606/9 |
| 5,304,169 | 4/1994 | Sand | 606/5 |
| 5,315,994 | 5/1994 | Guibert et al. | 607/101 |
| 5,334,193 | 8/1994 | Nardella | 606/41 |
| 5,342,357 | 8/1994 | Nardella | 606/40 |
| 5,348,554 | 9/1994 | Imran et al. | 606/41 |
| 5,366,443 | 11/1994 | Eggers et al. . | |
| 5,370,642 | 12/1994 | Keller | 606/9 |
| 5,374,265 | 12/1994 | Sand | 606/5 |
| 5,423,807 | 6/1995 | Milder | 606/20 |
| 5,423,811 | 6/1995 | Imran et al. | 606/41 |
| 5,437,662 | 8/1995 | Nardella | 606/40 |
| 5,458,596 | 10/1995 | Lax et al. | 606/31 |
| 5,462,521 | 10/1995 | Brucker et al. | 604/20 |
| 5,464,436 | 11/1995 | Smith | 607/89 |
| 5,496,312 | 3/1996 | Klicek | 606/50 |
| 5,507,790 | 4/1996 | Weiss | 607/100 |
| 5,569,242 | 10/1996 | Lax et al. | 606/42 |
| 5,681,282 | 10/1997 | Eggers et al. . | |
| 5,683,366 | 11/1997 | Eggers et al. . | |
| 5,692,058 | 11/1997 | Eggers et al. . | |
| 5,693,045 | 12/1997 | Eggers . | |
| 5,697,281 | 12/1997 | Eggers et al. . | |
| 5,697,536 | 12/1997 | Eggers et al. . | |
| 5,697,882 | 12/1997 | Eggers et al. . | |
| 5,697,909 | 12/1997 | Eggers et al. . | |

OTHER PUBLICATIONS

Danielson, C. "Thermal stability of reconstituted collagin fibrils, shrinkage characteristics upon in vitro maturation", Mechanisms of Ageing and Development, vol. 15, pp. 269–278, (1981).

Kronick, et al. "the locations of collagens with different thermal stabilities in fibrils of bovine recticular dermis". Connective Tissue Research, vol. 18, pp. 123–134, (1988).

Mainster, M.A. "Ophthalmic applications of infrared lasers—thermal considerations", Visual Sci., pp. 414–420, Ap. 1979.

Pearce, et al. "Kinetic models of laser–tissue fusion processes", ISA, paper #93–044, pp. 355–360, (1993).

Adrian, R. M. Treatment of Facial Telangiectasia Using the VersaPulse® Variable Pulse Width Frequency Doubled Neodymium: YAG Laser: A Case Report, Feb. 1994.

Chess, C.; Chess, Q. "Cool Laser Optics Treatment of Large Telangiestasia of the Lower Extremities." *J. Dermatol Surg Oncol.* 1993; 19:74–80.

Coulson, W. F. et al. "Nonablative Laser Treatment of Facial Rhytides: Animal Study." Abstract of BiOS '98 Symposium Conference: bo05—Cutaneous Applications of Lasers, 24–30 Jan. 1998, San Jose, CA.

Kincade, K. "Demand for Laser Resurfacing Soars: Quicker Healing, Less Risk of Scarring" *Dermatology times.* 1995. 16(10).

Fitzpatrick, R. "Treatment of Wrinkles with the UltraPulse $CO_2$ Laser." May 1995.

Laser Aesthetics, Inc. "The Cool Touch Laser." Brochure. May 1995.

Laser Aesthetics, Inc. "Cool Touch Model 130 Technical Specifications." Brochure.

National Health Communications, Inc. "New Laser Eliminates 'Lipstick Bleed'" Press Release Jul. 1993.

APPARATUS FOR CONTROLLED CONTRACTION OF COLLAGEN TISSUE

This application is a divisional of application Ser. No. 08/435,544, filed May 5, 1995, now U.S. Pat. No. 5,660,836.

CROSS-REFERENCE TO RELATED CASES

The present application is related to U.S. patent application Ser. No. 08/435,822, filed May 5, 1995, now U.S. Pat. No. 5,755,753, entitled "Method and Apparatus for Controlled Contraction of Collagen Tissue", having same named inventor Edward W. Knowlton.

BACKGROUND OF THE INVENTION

1. Field of the Invention

This invention relates generally for achieving contour sculpting and more particularly to a method and apparatus that creates a reverse thermal gradient in order to achieve contour sculpting through partial denaturation of collagen without ablation of the collagen and without affecting the melanocytes and other epithelial cells.

2. Description of Related Art

The skin is the one organ of the body that is readily available for inspection by the eyes and fingers of every living person. It is subjected to considerable abuse such as exposure to extreme environmental of cold, heat, wind, and sun.

The surface layer of the skin is called the epidermis. It is the barrier that prevents most substances from entering the body from outside while preventing body fluids from entering equilibrium with the environment. The basilar layer of the epidermis includes the melanocytes and other epithelial cells.

The melanocytes are small cells with a small, dark staining nucleus and a clear cytoplasm. Melanin in packaged in distinctive granules is produced by these cells and transferred then air dendritic processes to adjacent keratinocytes. The purpose of melanin is to protect the skin from the ravages of ultraviolet radiation. Beneath the epidermis is the papillary dermis and reticular dermis. Collagen tissue is found in the dermal and the sub dermal tissues.

There has been a large market for tightening the skin in order to reduce aging effects and effects created by exposing the skin to extreme environmental forces. To date there are two primary methods for tightening skin. The first is surgical skin excision. The second is chemical bum. When skin is surgically excised it leaves large scares. This is generally not a satisfactory solution for many skin tightening applications. With chemical peel treatments the process is painful, there is damage to the melanocytes and other epithelial cells, the patient maybe have spotted pigmentation, or with most of the melanocytes and other epithelial cells destroyed the patient can have a predominately white complexion. In the chemical peel method a thermal gradient is created which is hotter at the surface of the epidermis and cooler at the sub dermal layers. With the creation of this type of thermal gradient there is a great likelihood of modification or destruction of the melanocytes and other epithelial cells, resulting in blotchiness or an inability to tan in the future.

Collagen molecules are produced by fiborblasts which synthesize three polypeptide chains that wrap around one another in a triple helix. Each of the chains is approximately 1000 amino acid units in length, with glycine recurring regularly every third unit and hydroxyproline and proline recurring very frequently. Cross-linking occurs between the side, not the ends, of collagen molecules and is coupled with the amino acid composition to give collagen its great strength. Collagen tissue shrinkage takes place in a direction parallel to an axis of collagen fibers.

The phenomenon of thermal shrinkage of collagen begins with a denaturization of the triple helix of the collagen molecule. Partial denaturization of collagen tissue results in a shrinkage of the collage and provides a "tightening" effect on the overlaying skin. To date there have been no devices or methods for contracting the underlying collagen tissue through partial denaturization without damaging the melanocytes and other epithelial cells in the epidermis.

Adipose tissue, more commonly known as fat, is formed of cells containing stored lipid. Adipose tissue is often subdivided into small lobules by connective collagen tissue serving as the fibrous septae.

Adipose tissue is widely distributed in the subcutaneous tissue but exhibits regional differences in amount partially because of age and sex. Excess adipose tissue can be physically undesirable from both health and cosmetic perspective. A current method for the removal of fatty tissue is the extraction of adipose tissue by liposuction. This is a purely mechanical method with undesirable side effects due to the invasive nature of the process.

Another method of removing fatty tissue is disclosed in U.S. Pat. No. 5,143,063 ("the '063"). The method of the '063 patent targets adipose tissue absorbs sufficient energy resulting in cell destruction and death. The method of the '063 patent fails to minimize damage to the melanocyte in the epidermis. Thus, with the method of the '063 patent can create unwanted blotchiness or changes in the melanocytes and other epithelial cells.

There exists the need for skin tightening without damaging the melanocytes and other epithelial cells, or without surgical intervention. There is a further need for non-surgically removing adipose tissue without damaging the melanocytes and other epithelial cells.

SUMMARY OF THE INVENTION

It is an object of the present invention to provide a method and apparatus for creating a reverse thermal gradient that utilizes one or more RF electrodes, an electrolytic solution to transfer RF energy from the RF electrodes to the epidermis and underlying layers, and wherein the apparatus includes a lumen adapted to receive a cooling fluid.

It is another object of the present invention to provide a method and apparatus for non surgically reducing loculations of fat without substantially damaging the melanocytes and other epithelial cells.

Another object of the present invention is to provide a method and apparatus for non surgically reducing loculations of fat with the use of a thermal energy source that does not substantially effect the melanocytes and other epithelial cells.

A further object of the present invention is to provide a method and apparatus for contour sculpture, by utilizing a reverse thermal gradient to partially denature collagen in fibrous septae tissue.

These and other objects of the invention are provided in an apparatus for applying radiant energy through the skin to an underlying subcutaneous layer, and deeper soft tissue layers, such as the muscle and overlying fascia, include loculations of fat with fibrous septae made of collagen tissue. Application of the radiant energy creates a desired contour effect without substantially modifying the melanocytes and other epithelial cells in the epidermis. The apparatus includes a membrane that conforms a contacting exterior surface of the membrane to a skin layer. One or more thermal electrodes are positioned in the membrane and create a reverse thermal gradient from the skin layer to the underlying collagen tissue. A focussing element focuses thermal energy to the underlying collagen tissue. The focussing element and the electrolytic solution create a reverse thermal gradient from the skin to the collagen tissue. A thermal power source is coupled to the thermal electrodes.

Further, a method of liposulpturing a layer under the skin comprised of a loculation of fat which has collagen tissue as a fibrous septae includes providing a membrane and a thermal energy source. A reverse thermal gradient is created which cools the top surface of the skin while heating the underlying loculation of fat. This is achieved without substantially modifying the melanocytes and other epithelial cells in the epidermis. Collagen tissue of the fibrous septae is partially denatured and contracted with a diminished destruction of cells.

Radiant energy is applied to a variety of different skin layers including the papillary dermis layer, the reticular dermis layer, and even to a subcutaneous layer and to underlying soft tissue. One suitable energy source is one or more RF electrodes. Electrolytic solution transfers RF energy from the RF electrodes to the underlying collagen tissue. The cooling fluid can create a reverse thermal gradient at the epidermis to underlying desired layers of about 30 degrees to about 80 degrees C. The apparatus can further include one or more thermal sensors positioned on the contacting exterior surface of the membrane, as well as one or more impedance monitors. Further, the apparatus can include a feedback device which is responsive to a detected characteristic of the skin or subcutaneous layer in order to provide a control delivery of RF energy from the RF electrodes. A variety of detected characteristics can be monitored including impedance measurements of the skin and temperature profiles of the skin.

The feedback device can also include a controller as well as a multiplexer.

The creation of the reverse thermal gradient provides for the controlled contraction of collagen tissue, e.g., partial denaturization of the collagen molecules that results in a shrinkage of the collagen tissue, which then extends to a shrinkage of the skin. Creation of the reverse thermal gradient is different from other methods of collagen contraction which typically employ a thermal gradient that has a higher temperature at the surface and decreases with the depth of penetration.

The apparatus of the present invention that creates the desired contour effect by the modification of collagen tissue surrounding loculations of fat can include a focussing element to help direct the energy past the epidermis and into the fat containing layers. The apparatus can further include a coupling device that couples the focussing element to the membrane, as well as a bracket which is positioned around the periphery of the membrane and also supports the focussing elements. Instead of killing cells, thermal lipolysis is utilized with a cooling blanket on the skin so that thermal destruction fat cells, and the melanocytes and other epithelial cells are minimally damaged.

A variety of thermal energy sources can be employed. Suitable energy sources include but are not limited to RF, microwave, ultrasound and the like. In one embodiment, the preferred energy source is RF.

DETAILED DESCRIPTION

The present invention provides an apparatus for applying radiant energy through the skin to underlying collagen tissue without substantially modifying the melanocytes and other epithelial cells found in the epidermis.

The present invention also provides an apparatus for applying radiant energy through the skin to underlying subcutaneous or deeper soft tissue layers that include loculations of fat with fibrous septae made of collagen tissue. Application of the radiant energy creates an desired contour effect of the loculations of fat without substantially modifying the melanocytes and other epithelial cells in the epidermis. Further, non invasive methods are providing for skin tightening and tightening the fibrous septae around the loculations of fat to create the desired contour effect.

The methods of the present invention do not provide for total necrosis of cells. Instead, with the method and apparatus creating the desired contour effect, the loculations of fat with the fibrous septae made of collagen tissue use a reverse thermal gradient applied to the underlying collagen tissue layers resulting in a partial denaturization of the collagen permitting it to become tightened. This is achieved without killing all of the fat cells within the loculations.

Various types of radiant energy can be utilized with the present invention. Radiant energy may be any kind that can cause cell heating or physical destruction by being applied to collagen tissue. Examples of suitable radiant energy source include, but are not limited to RF, microwave, ultrasound, and the like.

Figure 1:
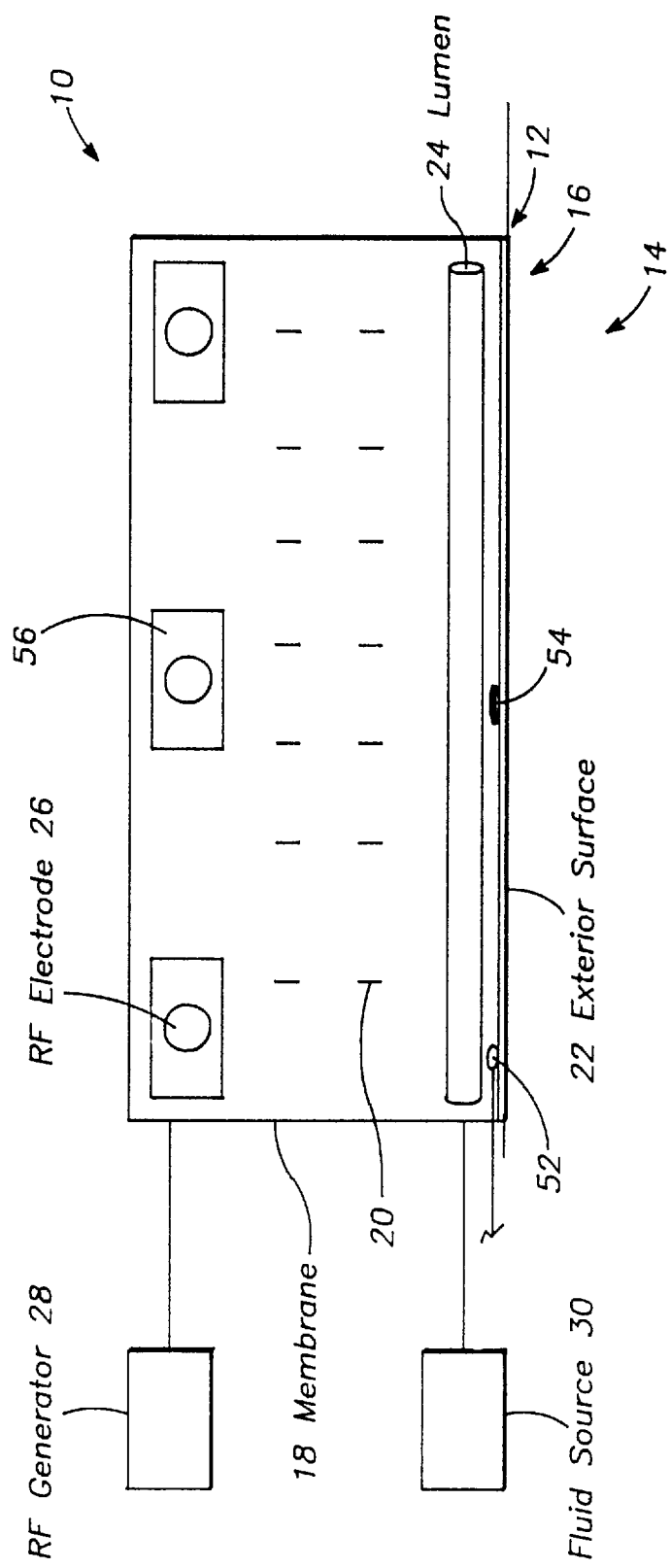
FIG. 1 is a perspective view of an apparatus for applying radiant energy through the skin in order to cause a partial denaturization of collagen tissue, resulting in a tightening of the skin.

Referring now to FIG. 1, an apparatus 10 applies radiant energy through a skin layer 12, such as the epidermis, and to the underlying collagen tissue 14 without substantially modifying melanocytes and other epithelial cells 16 found in the lower layer of epidermis layer 12.

A porous membrane 18 is adapted to receive an electrolytic solution 20. Porous membrane 18 becomes inflated to substantially conform a contacting exterior surface 22 of porous membrane 18 which is in close thermal contact with epidermis 12. Porous membrane 18 includes a cooling lumen 24 for receiving a cooling fluid that imparts a cooling effect on epidermis layer 12.

One or more thermal electrodes 26 are positioned at various places in porous membrane 18. In one embodiment, thermal electrodes 26 are positioned on a side that is substantially opposing to contacting exterior surface 22. In other embodiments, thermal electrodes 26 are placed closer to cooling lumen 24. In embodiment particularly suitable for the hips, porous membrane is about 20 cm by 30 cm, with an oval shape.

A thermal power source 28 is coupled to thermal electrodes 26 and a source of electrolytic solution 30 is coupled to porous membrane 18.

Figure 2:
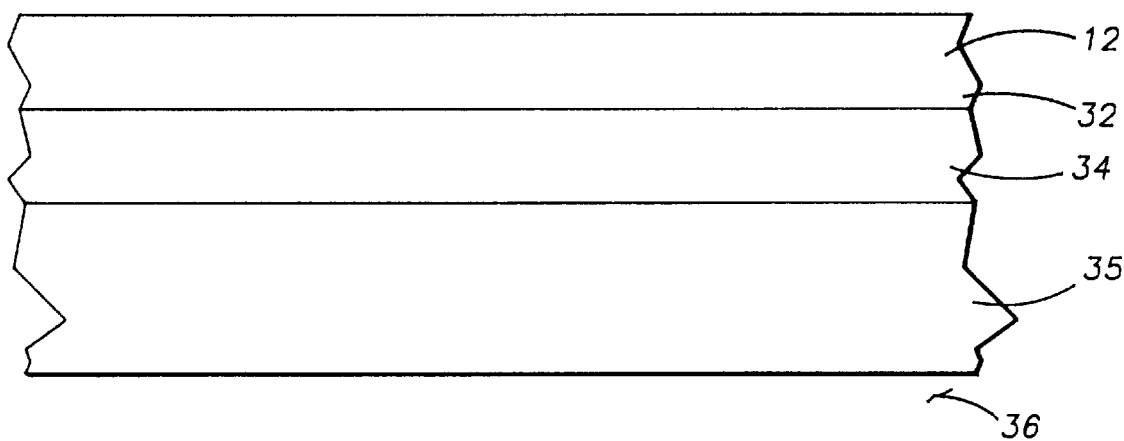
FIG. 2 is a cross-sectional view of the skin and underlying tissue.

With referenced now to FIG. 2, radiant energy can be applied through epidermis layer 12, to papillary dermis layer 32, to reticular dermis layer 34, to subcutaneous layer 35, as well as to underlying soft tissue 36. The extend of collage in the various layers is <5% in the epidermis, ~50% in the dermis, ~20% in the subcutaneous, ~5% in the muscle with overlying fascia. Shrinking of collagen tissue takes place in a direction parallel to the axis of the collagen fibers. Thermal shrinkage of collagen begins with the denaturization of the triple helix structure of the collagen fibers. This occurs when thermal energy is applied to the collagen tissue causing the hydrolysis of heat labial cross links of the collagen network.

Figure 3:
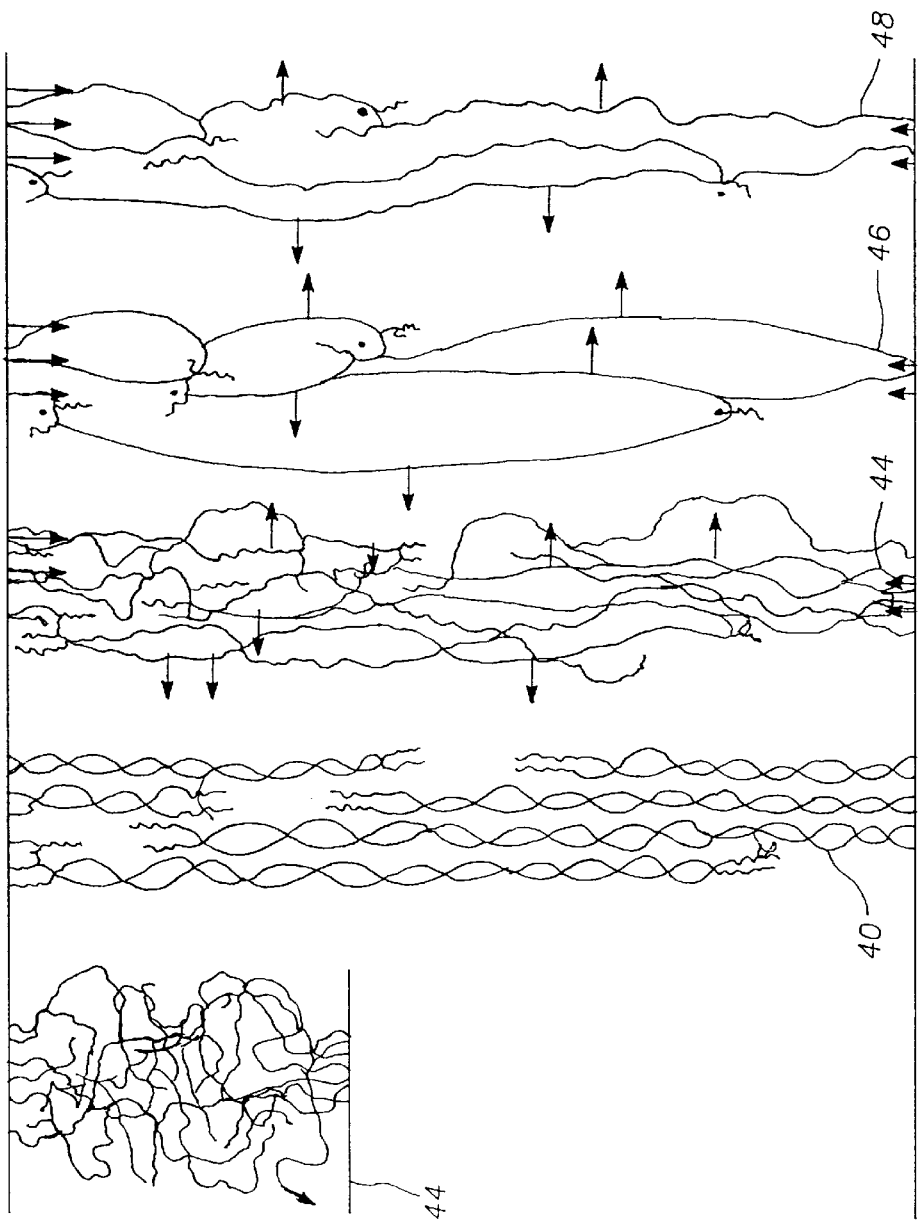
FIG. 3 is a schematic representation of the collagen network.

FIG. 3 is a schematic representation of a collagen network behavior under the influence of heat. The thickened lines represent the chains originally bound by covalent cross links. The arrows indicate tensions exerted on the collagen chains by the effect of heat. More particularly, FIG. 3 illustrates (i). native collagen network 40, (ii). collagen 42 under isometric conditions, (iii). collagen network without any restraint, (iv). collagen network 46 under isometric tension as long as the nodes are stable, and (v). collagen network 48 under isometric tension after some cross links have been cleaved.

In one embodiment of the present invention, thermal electrodes 26 are RF electrodes which can be a single electrode, or a plurality which can form a segmented flexible circuit. Thermal power source 28 is then an RF generator. Electrolytic solution 20 is introduced into porous membrane 18 and passes by RF electrodes 26. Electrolytic solution 20 transfers RF power from RF electrodes 28 to the desired underlying collagen tissue to achieve partial denaturization of the collagen molecule.

Generally, RF electrodes 26 can be monopular or bipolar. In the monopular mode, RF current flows through body tissue from a return electrode which can be in a form of a conductive pad applied to the patients outer skin. Maximum heating occurs where the current density is the greatest.

During a treatment phase, the denaturization of collagen molecules can be conducted under feedback control. Treatment can occur without the attention of medical supervision. Feedback is accomplished by (i). visualization, (ii). impedance, (iii). ultrasound, or (iv). temperature measurement. Optionally included and preferably positioned on contacting exterior surface 22 can be one ore more thermal sensors 52, as well as one or more impedance monitors 54. Thermal sensors 52 permit accurate determination of the surface temperature of epidermis layer 12.

Electrolytic solution 20 can be preheated to a selected temperature and modified as necessary. This reduces the amount of time needed to effect at satisfactory denaturization of collagen molecules and subsequent skin tightening.

Porous membrane 18 can be made of a material that is an insulator. For purposes of this disclosures, an insulator is a barrier to thermal or electrical energy flow. Porous membrane 18 can be made of a material which permits controlled delivery of electrolytic solution 20 to epidermis layer 12. Porous membrane 18 can be made of a variety of materials including, but not limited to knitted polyester, continuous filament polyester, polyester-cellulose, rayon, polyamide, polyurethane, polyethylene and the like. Suitable commercial products include, (i). Opcell available from Centinal Products Corp., Hyannis, Mass., and (ii). UltraSorb, HC 4201 or HT 4644 MD from Wilshire Contamination Control, Carlsbad, Calif. Pockets or zones 56 can be formed around RF electrodes 26. Each pocket 56 has a lower porosity for the flow of electrolytic solution 20 than all other sections of porous membrane 18. Differences in porosity can be achieved with different types of materials which form porous membrane 18. Electrolytic solution 20 is retained in pockets 56 longer than in non-pocket sections of porous membrane 18, and there is a greater transfer of RF energy to electrolytic solution 20, creating a larger electrode. The larger electrode produces RF and thermal energy to create a larger electrode effect. However, this does not effect the creation of the reverse thermal gradient. RF energy is still transferred through porous membrane 18 passing in the vicinity of cooling lumen 24, in order to create a lower temperature at epidermis layer 12 and the temperature increases as deeper layers are reached.

Figure 4:
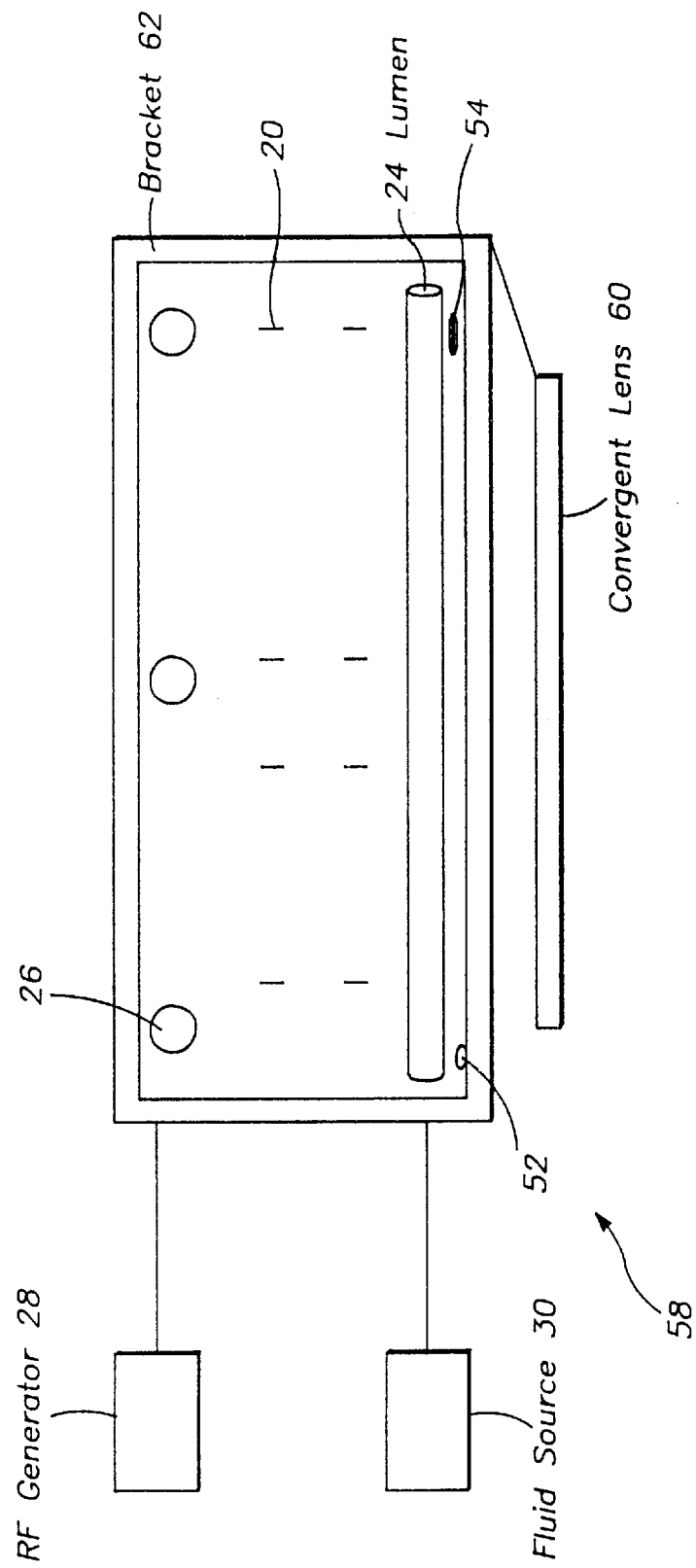
FIG. 4 is a schematic diagram of an apparatus for applying radiant energy to underlying subcutaneous layers or deeper soft tissue layers to create a desired contour effect by partially denaturing collagen tissue, and without substantially modifying melanocytes and other epithelial cells in the epidermis.
Figure 5:
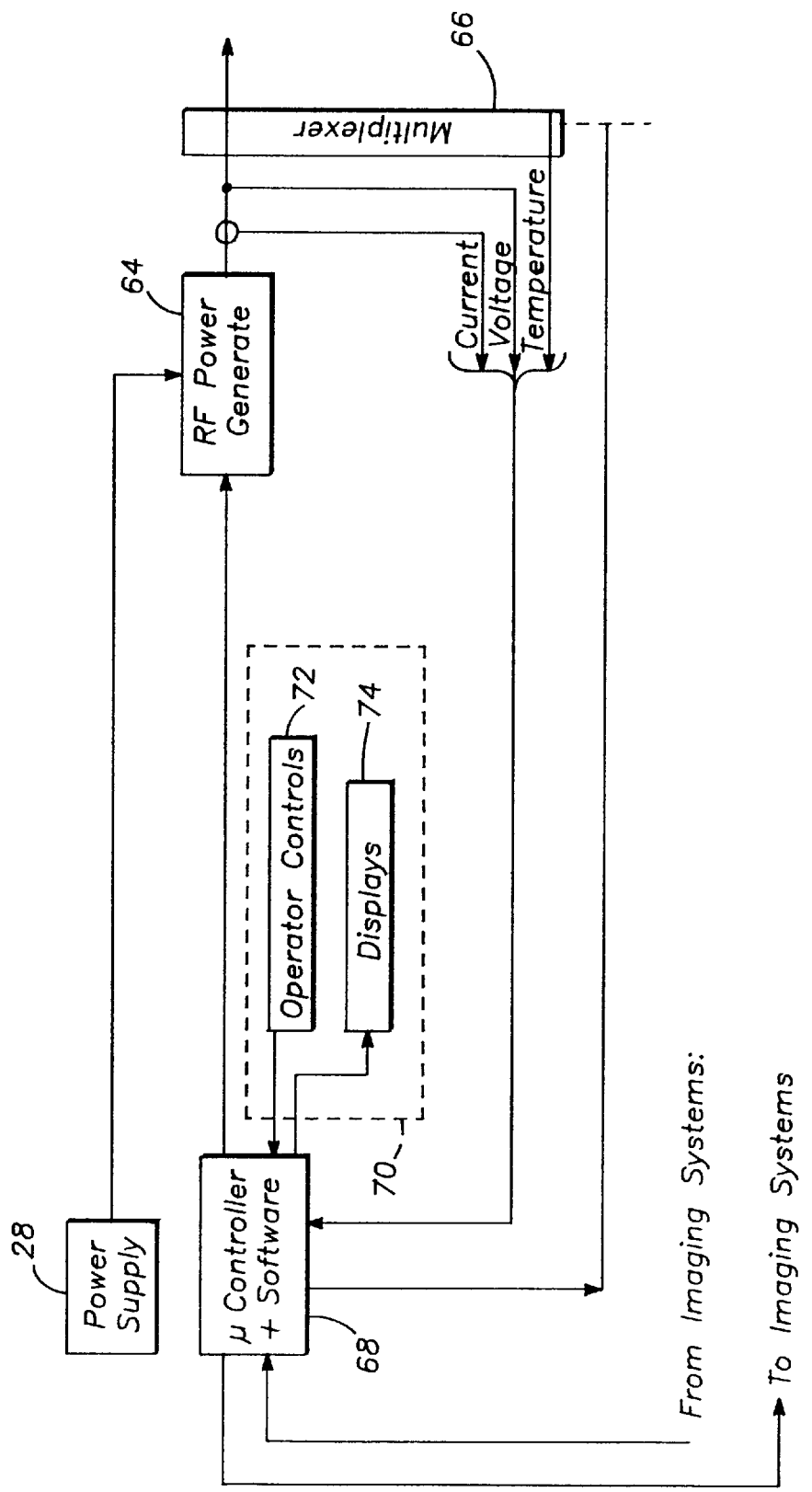
FIG. 5 is a block diagram of an RF system which can be utilized with the present invention.

Referring now to FIG. 4, an apparatus 58 for creating a desired contour effect of underlying subcutaneous layers or deeper soft tissue layers which include loculations of fat with fibrous septae made of collagen tissue is illustrated. The apparatus 58 of FIG. 4, includes a porous membrane 18, electrolytic solution 20, a contacting exterior surface 22, a cooling lumen, thermal electrodes 26, a thermal power source 28, an electrolytic solution source 30, one or more thermal sensors 52, as well as one or more impedance monitors 54. Apparatus 58 also includes a focussing element 60 which focuses thermal energy from electrolytic solution 20 to the underlying collagen tissue. Focussing element 60 and electrolytic solution 20 create a reverse thermal gradient from epidermis layer 12 to the underlying collagen tissue 14. Focussing element 62 can be, in the case of ultrasonic energy, a lens having a flat planer surface on the radiation wave incident side and a concave exit face, see *Ultrasonics Theory and Application,* by G. L. Goberman, Heart Publishing Co., New York (1959), at section 2.6. The use of such a focussing lens for ultrasonic energy with a planer wave receiving face and concave exit face is also described in the article "Deep Local Hypothermia for Cancer Therapy: Extreme Electromagnetic and Ultrasound Technics," A. Y. Cheung and A. Neyzari, *Cancer Research,* Vol. 44, pp.4736–4744, October 1984.

Radio frequencies can be the thermal energy source, and various localizing technique, well known in the art, can be utilized. In one embodiment, radio frequency energy is supplied by capacitive coupling directly to epidermis layer 12 for areas close to the dermal tissue. Radio frequency induction focussing can be achieved with the use of plural focussing coils which are adaptive at the zone of interest and are elsewhere subtractive. Alternatively, radio frequency energy may be focused by having a multiple beam phased array. For concave focussing see, "Tumor reduction by radio frequency therapy response", H. H. Lavien et al., *JAMA, Vol.* 233, at 2198–2200.

Alternative radio frequency focussing methods are disclosed in "Equipment for Local Hypothermia Therapy of Cancer", C. F. Babbs et al., *Medical Instrumentation,* Vol. 16, No. 5, Sept–Oct 1982, pp.245–248.

It will be appreciated that focussing element 60 can be a convergent lens. Further, focussing element 60 can be positioned in porous membrane 18, and at the exterior 16 between epidermis layer 12 and porous membrane 18. Further, a coupling device 62 can be included which couples focussing element 60 with porous membrane 18. In one embodiment, coupling device 62 is a bracket which is positioned around a periphery of porous membrane 18, and supports focussing element 50 in relation to porous membrane 18.

In the method for tightening skin, porous membrane 18 and thermal energy source 26 are provided. A reverse thermal gradient is created which cools a surface of epidermis layer 12 while heating underlying collagen containing layers. Epidermis layer 12 as well as underlying collagen containing tissue are heated, without substantially effecting the melanocytes and other epithelial cells in epidermis layer 12, resulting in a denaturization of collagen molecules, causing a contraction of the collagen tissue and a tightening of the skin. This method can be applied numerous times. In many instances, it may be desirable to tighten the skin to a certain level and then in subsequent treatments the skin is tightened further. There are may be four fine treatments to fine tune the contour effects with greater precision. In this method, collagen containing tissue is partial denatured and fat cell destruction is minimized. This is achieved by partially denaturing by cleaving heat labial cross links of the collagen molecules.

The reverse thermal gradient provides a variation in temperature throughout the various tissue layers. For example, in one embodiment, the reverse thermal gradient is a temperature range from about 30 degrees to about 80 degrees C., initiating from epidermis layer 12 to collagen containing tissue layers. The reverse thermal gradient can have a temperature range of about 30 to 75 degrees C., and additionally from about 30 to 70 degrees C.

In another embodiment, a method for liposculpturing an area of the body where there is an underlying area comprised of a loculation of fat that has collagen tissue as a fibrous septae also includes creating a reverse thermal gradient from epidermis layer 12 to the desired underlying loculation of fat layer. Sufficient thermal energy is supplied through epidermis layer 12, without damaging or substantially modifying the melanocytes and other epithelial cells, through other skin layers and is focused on the collagen tissue of the fibrous septae. Thermal energy partially denatures the collagen tissue with a minimal destruction of fat cells. Again, this is achieved by partially denaturizing, e.g., by cleaving, heat labial cross links of collagen molecules. The reverse thermal gradient produces a net mobilization of intra-cellular fat with diminished destruction of fat cells.

For purposes of illustration, without the scope of the invention let it be assumed that power source 28 is an RF power source, an RF power source 28, feeds energy to an RF power generator 64 and then to RF electrodes 26. A multiplexer 66 measures current, voltage and temperature, at the numerous thermal sensors associated with to each RF electrode 26. RF electrodes 26 can be individually measured. Multiplexer 66 is driven by a controller 68 which can be a digital or analog controller, or a computer with software. When controller 68 is a computer it can include a CPU coupled through a system bus. On the system can be a keyboard, disk drive, or other non volatile memory systems, a display, and other peripherals, as are well known in the art. Also coupled to the bus are a program memory and a data memory.

An operator interface 70 includes operator controls 72 and a display 74. Controller 68 can be coupled to different types of imaging systems including ultrasonic, thermal sensors 52, and impedance monitors 54.

Current and voltage are used to calculate impedance. A diagnostic phase can be initially run to determine the level of treatment activity. This can be done through ultrasound as well as other means. Diagnostics can be performed both before and after treatment.

Thermal sensors 52, and thermal sensors 76 contained within RF generator 64 measure voltage and current that is delivered to the desired treatment site. The output for these sensors is used by controller 68 to control the delivery of RF power. Controller 68 can also control temperature and power. An operator set level of power and/or temperature may be determined and this will not be exceeded. Controller 68 maintains the set level under changing conditions. The amount of RF energy delivered controls the amount of power. A profile of power delivered can be incorporated in controller 68, as well as a preset amount of energy to be delivered. Feedback can be the measurement of impedance, temperature, or other indicators and occurs either at control 68 or at RF generator 64, if it incorporates a controller. For impedance measurement, this can be achieved by supplying a small amount of non therapeutic RF energy. Voltage and current are then measured to confirm electrical contact.

Circuitry, software and feedback to controller 68 result in full process control and are used to change, (i). power, (ii). the duty cycle, (iii). monopular or bipolar energy delivery, (iv). electrolytic solution 20 delivery, flow rate and pressure and (v). can determine when the process is completed through time, temperature and/or impedance. These process variables can be controlled and varied based upon tissue temperature monitored at multiple sites on contacting exterior surface 22 as well as monitoring impedance to current flow at each RF electrode 26, indicating changes in current carrying capability of the tissue during the process. Further, controller 68 can provide multiplexing, monitor circuit continuity, and determine which RF electrode 26 is activated.

Figure 6:
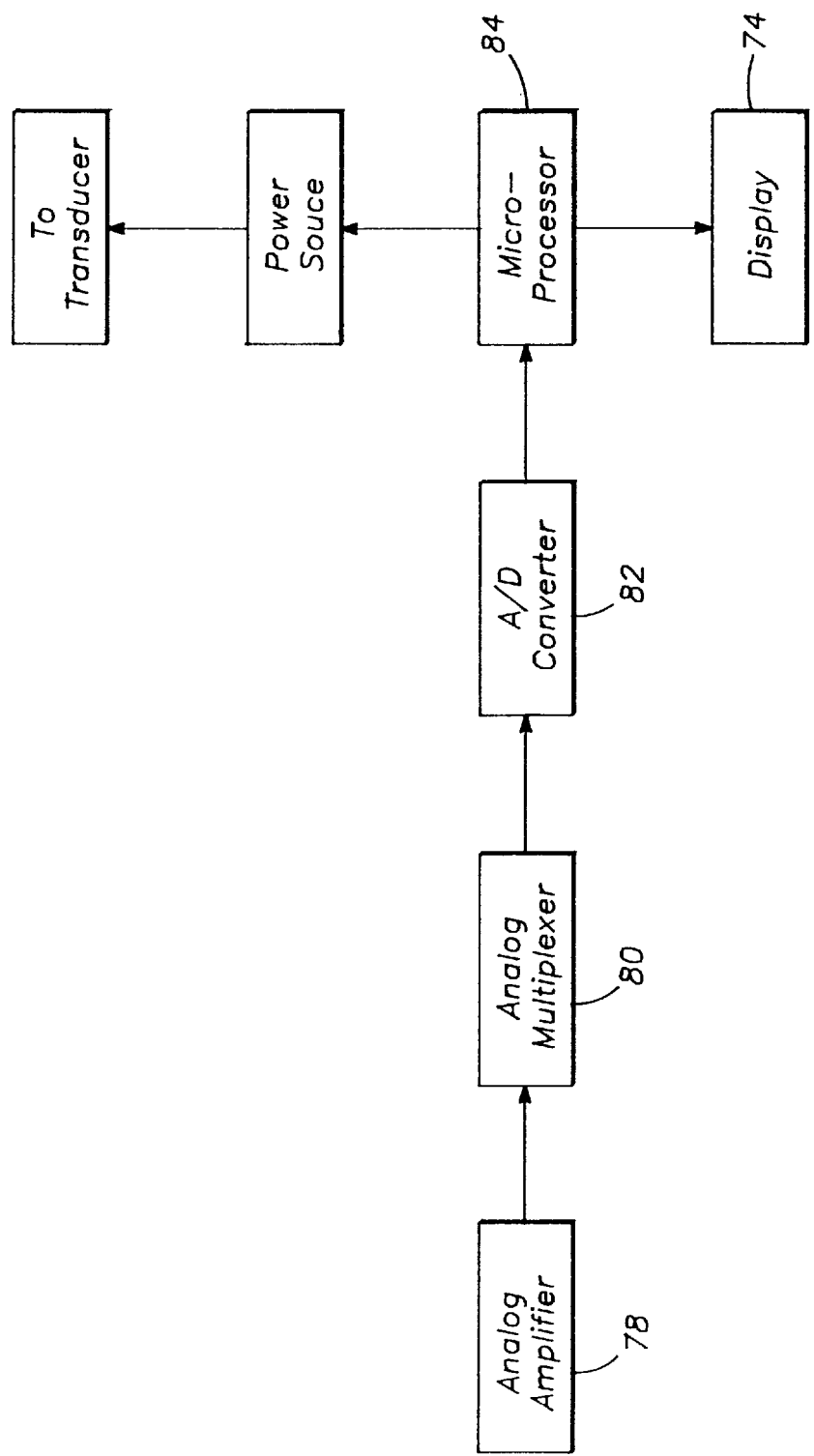
FIG. 6 is a block diagram of processing circuit of one embodiment of the invention.

A block diagram of one embodiment of suitable processing circuitry is shown in FIG. 6. Thermal sensors 52 can be thermistors which have a resistance that varies with temperature. Analog amplifier 78 can be a conventional differential amplifier circuit for use with thermistors and transducers. The output of analog amplifier is sequentially connected by an analog multiplexer 80 to the input of an analog digital converter 82. The output of amplifier 78 is a voltage which represents the respective sensed temperatures. The digitized amplifier output voltages are supplied by analog to digital converter 82 to a microprocessor 84. Microprocessor 84 calculates the temperature or impedance of the tissue. Microprocessor 84 can be a type 6800. However, it will be appreciated that any suitable microprocessor or general purpose digital or analog computer can be used to calculate impedance or temperature.

Microprocessor 84 sequentially receives and stores digital representations of impedance and temperature. Each digital value received by microprocessor 84 corresponds to different temperatures and impedances.

Calculated temperature and impedance values can be indicated on display 74. Alternatively, or in addition to the numerical indication of temperature or impedance, calculated impedance or temperature values can be compared by microprocessor 84 with temperature and impedance limits. When the values exceed predetermined temperature or impedance values a warning can be given on display 74 and additionally, the delivery of RF energy to its respective electrode can be decreased or multiplexed to another electrode. A control signal from microprocessor 84 can reduce the power level by RF generator 64, or deenergize the power delivered to any particular electrode. Controller 68 receives and stores the digital values which represent temperatures and impedances. Calculated surface temperatures and impedances can be forwarded by controller 68 to display 74. If desired, the calculated surface temperature of epidermis layer 12 is compared with a temperature limit and a warning signal can be sent to display 74. Similarly, a control signal can be sent to RF power source 26 when temperature or impedance values exceed a predetermined level.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

I claim:

1. An apparatus for applying energy through a skin epidermis surface to an underlying subcutaneous layer or deeper soft tissue layers that includes loculations of fat with fibrous septae made of collagen containing tissue, to create a desired contour effect without substantially modifying melanocytes in an epidermis, comprising;

a membrane that conforms a contacting exterior surface of the membrane to the skin epidermis surface, one or more electrodes positioned in the membrane configured to be coupled to an energy source;

an electrolytic media positioned in the membrane and coupled to the electrodes to receive energy from the electrodes and transfers energy from the electrodes to the skin epidermis surface; and a focussing element that creates a reverse thermal gradient from the skin epidermis surface to the collagen containing tissue.

2. The apparatus of claim 1, wherein the focussing element is positioned in the membrane.

3. The apparatus of claim 1, wherein the focussing element is positioned at an exterior of the membrane between the skin layer and the membrane.

4. The apparatus of claim 3, further comprising:

a coupling device that couples the focussing element to the membrane.

5. The apparatus of claim 3, further comprising:

a bracket positioned around a periphery of the membrane, and supporting the focussing element.

6. The apparatus of claim 1, further comprising:

a fluid passage lumen positioned in the membrane to cool a surface of the skin, the membrane receiving electrolytic solution which transfers energy from the electrodes to the skin and a subcutaneous layer; and a source of electrolytic solution coupled to the fluid passage lumen.

7. The apparatus of claim 1, wherein energy is applied through a papillary dermis layer.

8. The apparatus of claim 1, wherein energy is applied through a reticular dermis layer.

9. The apparatus of claim 1, wherein energy is applied through a subcutaneous layer and deeper soft tissues.

10. The apparatus of claim 1, wherein the electrodes arc RF electrodes, the energy source is an RF power source, and the electrolytic media transfers RF energy from the RF electrode to the underlying collagen containing tissue.

11. The apparatus of claim 10, further comprising a feedback device responsive to a detected characteristic of the skin or subcutaneous layer that provides a controlled delivery of RF energy to one or more plurality of RF electrodes.

12. The apparatus of claim 11, wherein the detected characteristic is an impedance measurement of the skin.

13. The apparatus of claim 11, wherein the detected characteristic is a temperature profile of the skin.

14. The apparatus of claim 11, wherein the feedback device includes a controller.

15. The apparatus of claim 11, wherein the feedback device includes a multiplexer.

16. The apparatus of claim 1, further comprising:

a cooling fluid source coupled to a cooling lumen.

17. The apparatus of claim 16, wherein the cooling fluid source houses water.

18. The apparatus of claim 1, wherein the membrane is a microporous membrane.

19. The apparatus of claim 1, wherein the membrane conforms closely to the surface of the skin.

20. The apparatus of claim 1, wherein the apparatus includes a plurality of RF electrodes.

21. The apparatus of claim 1, further comprising:

one or more thermal sensors positioned on the contacting exterior surface of the membrane.

22. The apparatus of claim 1, further comprising:

one or more impedance monitors positioned on the contacting exterior surface of the membrane.

23. The apparatus of claim 1, wherein the focussing element maintains a temperature of the skin epidermis surface at a lower temperature than a temperature of the underlying collagen containing tissue.

24. The apparatus of claim 23, wherein the focussing element includes a cooling medium delivery device coupled to the membrane.

25. An apparatus for liposculpturing an area of a body including a skin surface with multiple layers, and an underlying are made of a loculation of fat that has collagen containing tissue as a fibrous septae, comprising:

an energy delivery device means;

electrolytic media energy delivery means coupled to the energy delivery device means to receive electrolytic energy and transfer the electrolytic energy from the energy delivery device means to the skin surface, the electrolytic media means delivering energy to the skin surface and the energy passing through the skin surface to the underlying collagen containing tissue to contract at least a portion of the collagen containing tissue while minimizing cellular destruction and creating a tightening the skin surface; and a membrane housing means housing at least a portion of the energy delivery device means, the membrane means including a membrane skin surface interface means.

26. The apparatus of claim 25, wherein the energy delivery device means includes a thermal energy delivery means positioned in the membrane means and delivering thermal energy to the electrolytic media means.

27. The apparatus of claim 26, further comprising:

a focussing element temperature maintenance means that maintains a temperature of the skin surface at a lower temperature than a temperature of the underlying collagen containing tissue.

28. The apparatus of claim 27, wherein the focusing element temperature maintenance means is positioned in the membrane means.

29. The apparatus of claim 27, wherein the focussing element temperature maintenance means is positioned at an exterior of the membrane means between the skin surface and the membrane skin interface surface means.

30. The apparatus of claim 25, further comprising:

an electrolytic source electrolytic media delivery means coupled to the membrane means to deliver the electrolytic media means to the membrane means.

31. The apparatus of claim 25, wherein the energy delivery device means is an RF delivery means.

32. The apparatus of claim 25, further comprising:

an impedance monitor means coupled to the energy delivery device means.

33. The apparatus of claim 25, further comprising:
a thermal sensor means coupled to the energy delivery device means.

34. The apparatus of claim 25, further comprising:
a feedback device energy means coupled to a thermal sensor means and the energy delivery device means and responsive to a detected characteristic of the collage containing tissue to deliver controlled energy to the energy delivery device means.

35. The apparatus of claim 34, wherein the feedback device means includes a controller means.

36. The apparatus of claim 35, wherein the feedback device means includes a multiplexer means.

37. The apparatus of claim 25, wherein the energy delivery means is a microwave means.

38. The apparatus of claim 25, wherein the energy delivery means is an ultrasound means.

* * * * *